United States Patent [19]

Cumming

[11] Patent Number: 4,634,773

[45] Date of Patent: Jan. 6, 1987

[54] THIAZOLIDINYLETHYLCHLOROCAR-BONATES

[75] Inventor: William J. Cumming, North Chelmsford, Mass.

[73] Assignee: Polaroid Corporation, Cambridge, Mass.

[21] Appl. No.: 742,927

[22] Filed: Jun. 10, 1985

Related U.S. Application Data

[62] Division of Ser. No. 514,700, Jul. 18, 1983, abandoned.

[51] Int. Cl.$^4$ ............................................. C07D 277/04
[52] U.S. Cl. .................................... 548/146; 548/200; 548/201
[58] Field of Search ........................ 548/146, 200, 201

[56] References Cited

U.S. PATENT DOCUMENTS

| | | | |
|---|---|---|---|
| 3,719,489 | 3/1973 | Ciechiuch | 96/29 D |
| 4,073,918 | 2/1978 | Metz | 548/201 |
| 4,098,783 | 7/1978 | Ciechiuch | 96/29 D |
| 4,468,450 | 8/1984 | Meneshini | 430/222 |

OTHER PUBLICATIONS

Babad, Chem. Reviews, 73 p. 75 (1973).

*Primary Examiner*—Robert Gerstl

[57] ABSTRACT

This invention relates to 2-(thiazolidin-2'-yl) ethylchlorocarbonates useful as intermediates in the synthesis of photographic image dye-providing materials and to their preparation by the reaction of the appropriate 2-(2'-hydroxyethyl)-thiazolidine with phosgene under certain conditions.

5 Claims, No Drawings

THIAZOLIDINYLETHYLCHLOROCARBONATES

This is a divisional of application Ser. No. 514,700, filed July 18, 1983 now abandoned.

FIELD OF THE INVENTION

This invention relates to 2-(thiazolidin-2'-yl)ethylchlorocarbonates and to the synthesis thereof.

BACKGROUND OF THE INVENTION

U.S. Pat. No. 3,719,489 describes and claims photographic processes employing certain photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color-providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group

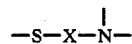

or —S—X—N= wherein X is

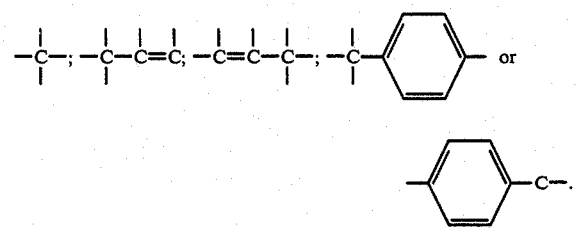

These 1,3-sulfur-nitrogen compounds may be linear or cyclic in structure, and in a particularly preferred embodiment are thiazolidine compounds, such as, compounds which comprise a dye radical having the chromophoric system of an azo, anthraquinone, phthalocyanine or other dye and a thiazolidin-2'-yl moiety which may be bonded directly to the dye radical or indirectly through an appropriate linking group.

U.S. Pat. No. 4,098,783, a continuation-in-part of Ser. No. 465,694, now abandoned, which is a division of said U.S. Pat. No. 3,719,489 discloses that dyes substituted with a thiazolidin-2'-yl moiety may be synthesized by condensing a dye possessing an aldehyde group with a 2-aminoethanethiol, or rather than forming the thiazolidin-2-yl moiety as the final step in the synthesis, an intermediate possessing an aldehyde group may be condensed with the selected 2-aminoethanethiol and the condensation product then reacted with the appropriate molecule or molecules to yield the final dye product. For example, an intermediate comprising a linking group substituted with a thiazolidin-2'-yl moiety may be synthesized from an appropriate aldehyde in several steps including the condensation with a 2-aminoethanethiol and the linking group then reacted with a dye radical.

Certain 2-(2'hydroxyethyl)-thiazolidines useful as intermediates in the synthesis of thiazolidine compounds such as those disclosed in aforementioned U.S. Pat. No. 4,098,783 form the subject matter of copending U.S. patent application Ser. No. 474,144 of Roberta R. Arbree, William J. Cumming and Frank A. Meneghini filed Mar. 10, 1983, now abandoned.

The present invention is concerned with another class of thiazolidine compounds useful as intermediates in the preparation of photographic image dye-providing materials and other photographically useful reagents and with the preparation of such intermediates.

SUMMARY OF THE INVENTION

It is, therefore, one object of the present invention to provide a certain class of compounds, namely, 2-(thiazolidin-2'-yl)ethylchlorocarbonates.

It is another object of the present invention to provide a method of preparing this class of compounds.

Other objects of this invention will in part be obvious and will in part appear hereinafter.

This invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

According to one embodiment of the present invention, it has been found that 2-(2'-hydroxyethyl)-thiazolidines including the hydrohalide salts thereof can be converted to the corresponding chlorocarbonate hydrochlorides under certain specific conditions, namely, by introducing a 2-(2'-hydroxyethyl)-thiazolidine, in increments, into a solution of phosgene (carbonyl chloride) dissolved in an inert organic solvent; allowing said hydroxyethyl thiazolidine to react with said phosgene between the introduction of successive increments while maintaining the temperature at about 0° C. or below; and preventing said hydroxyethyl thiazolidine from contacting gaseous phosgene during the introduction and reaction of each said successive increments.

It is quite surprising that the above-denoted reaction yields the thiazolidine chlorocarbonate and that the chlorocarbonate is obtained as the hyrochloride salt. As discussed in Chem. Reviews, 73, 75 (1973), phosgene reacts with alkyl tertiary amines at low temperatures to yield unstable crystalline complexes which decompose to the corresponding N,N-dialkylcarbamoyl chlorides when warmed to room temperature. Since the nitrogen of the thiazolidine is a tertiary amine and also capable of reacting with the phosgene, it is unexpected that the phosgene would react exclusively with the alcohol group, i.e., the 2'-hydroxyethyl group rather than with the thiazolidine nitrogen. Though such a reaction may be precluded by using a hydrohalide salt of the hydroxyethyl compound, the subject method avoids this problem. Perhaps the alcohol group reacts first or perhaps due to steric hindrance, the thiazolidine nitrogen picks up the HCl instead a phosgene molecule. Whatever the mechanism may be, the addition of small increments of the hydroxyethyl compound to a large excess of phosgene under the aforementioned conditions apparently inhibits carbonate ester formation to give the desired chlorocarbonate product.

Typical of the novel compounds that may be produced by the subject method are the 2-(thiazolidin-2'-yl)ethylchlorocarbonates of the formula

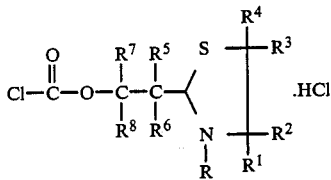

wherein R is selected from alkyl, aryl, aralkyl and alkaryl; $R^1$ is selected from hydrogen, carboxy, N,N-dialkylcarboxamido, alkyl, aryl, aralkyl and alkaryl; $R^5$ is selected from hydrogen and a group that can be removed upon cleavage of the thiazolidine ring to leave an electron pair, e.g., carboxy; and $R^2$, $R^3$, $R^4$, $R^6$, $R^7$ and $R^8$ each are selected from hydrogen, alkyl, aryl, aralkyl and alkaryl.

Typical aryl groups include phenyl and biphenyl and said alkyl groups comprising R, $R^1$, $R^2$, $R^3$, $R^4$, $R^6$, $R^7$ and $R^8$ usually contain 1 to 20 carbon atoms. Said aralkyl may be, for example, phenyl-substituted alkyl wherein said alkyl usually contains 1 to 20 carbon atoms, and said alkaryl may be, for example, alkyl-substituted phenyl wherein said alkyl usually contains 1 to 20 carbon atoms. When $R^1$ is N, N-dialkylcarboxamido, each alkyl usually contains 1 to 20 carbon atoms.

In carrying out the subject method, any dry inert organic solvent may be used for the phosgene solution. However, the solvent ordinarily employed is a hydrocarbon solvent, such as, benzene, toluene or hexane. For convenience, the 2-(2'-hydroxyethyl)-thiazolidine also is usually employed in solution in a dry hydroqarbon solvent, and the hydroxyethylthiazolidine solution added directly into the phosgene solution, i.e., below the surface of the phosgene solution to avoid contact with gaseous phosgene. The introduction of successive increments of hydroxyethylthiazolidine solution may be carried out, for example, by using a syringe or the like to introduce small aliquots underneath the surface of the phosphene solution and allowing each aliquot to react with the phosgene before adding the next aliquot. Besides using anhydrous conditions, the reaction temperature should be maintained at about 0° C. or below. Generally, about 5 to 6 moles of phosgene is employed for each mole of hydroxyethylthiazolidine, and thus, the concentration of the respective thiazolidine and phosgene solutions will be adjusted accordingly. As noted above, the hydroxyethyl-thiazolidines may be employed as their hydrohalide salts, e.g., the hydrochloride salts if desired.

Excess phosgene can be removed in a known manner by purging the reaction mixture with a dry, inert gas and allowing the purging effluent to pass through a solution of sodium hydroxide which will destroy the phosgene. The chlorocarbonate is then collected in any suitable and convenient manner, for example, by filtration and kept in a dry inert atmosphere.

The 2-(2'-hydroxyethyl)-thiazolidines used as the starting materials in the subject method may be those forming the subject matter of aforementioned U.S. patent application Ser. No. 474,144. These thiazolidines may be represented by the formula

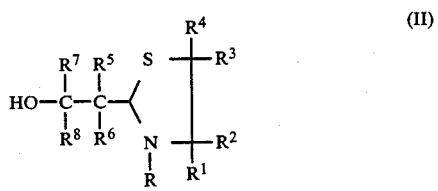

and as discussed in said application Ser. No. 474,144, they may be synthesized in a conventional manner by reacting the appropriate aldehyde with a 2-aminoethanethiol wherein the 2-amino group has one replaceable hydrogen atom. The aldehyde may be reacted as a dimer, e.g., the dimer of β-hydroxy-n-butyraldehyde, and the 2-aminoethanethiol may be reacted as a hydrochloride salt. Also, it may be desirable to conduct the reactions using such salts in the presence of triethylamine, sodium hydroxide or other reagent for neutralizing the hydrochloride and imparting enhanced solubility in the particular reaction medium employed.

Examples of aldehydes and 2-aminoethanethiols that may be employed in synthesizing the hydroxyethylthiazolidines of formula II are those having the following formulae

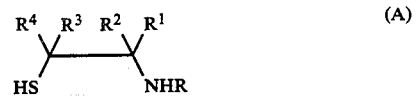

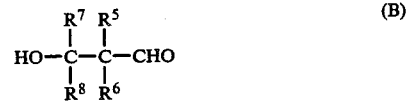

Such aldehydes and 2-aminoethanethiols are known compounds that may be synthesized in a conventional manner.

In formula II and in formulae A and B, the substituent groups R, $R^1$, Rhu 2, $R^3$, $R^4$, $R^5$, $R^6$, $R^7$ and $R^8$ may be unsubstituted or substituted with alkyl, alkoxy or other appropriate group which is unreactive under the conditions of the reaction.

The following example is given to further illustrate the present invention and is not intended to limit the scope thereof.

EXAMPLE

Preparation of the compound having the formula

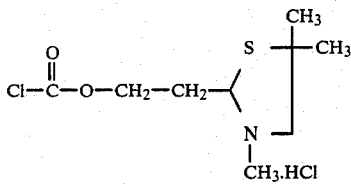

In a 125 ml round bottom flask was placed 50 ml of a benzene solution containing 12.5% phosgene (approximately 64 mmoles). The flask was fitted with a septum and magnetic stirrer and cooled to 0° C. Two grams (11.4 mmoles) of 1-methyl-2-(2′-hydroxyethyl)-5,5-dimethylthiazolidine having the formula

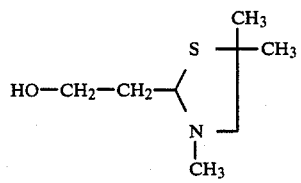

was dissolved in 10–15 ml of dry toluene and placed in a syringe. When the phosgene solution was cooled to 0° C., the solution of hydroxyethyl-thiazolidine was added in small aliquots by inserting the needle of the syringe through the septum and underneath the surface of the liquid and then withdrawing the syringe after each aliquot until addition was complete. The reaction mixture was stirred at 0° C. for an hour and allowed to come to room temperature. Then dry nitrogen was bubbled into the flask for an hour to displace excess phosgene, allowing the effluent to pass through sodium hydroxide solution to destroy the excess phosgene. The solid was collected from the de-phosgenated solution and washed with ether. Usually solid appears in the reaction solution as bubbling proceeds. If not, the de-phosgenated solution is concentrated to about one-half, filtered, the solid washed with ether, air dried and then placed in a dry storage container.

As noted above, it is essential to the success of the subject method to conduct the reaction of hydroxyethylthiazolidine and phosgene under certain conditions as described above. For example, little if any of the desired product was obtained using the following procedure.

20 ml of dry toluene, 7 g (50 mmoles) of potassium carbonate (finely ground and heated at 140° C. for one hour) and 1 g (5.7 mmoles) of 1-methyl-2-(2′-hydroxyethyl)-5,5-dimethyl-thiazolidine were combined in a flamed flask under nitrogen. After cooling to −78° C., 17 ml of a 12.5% solution of phosgene in benzene (24 mmoles COCl₂) was added dropwise over 30 mintues. When addition was complete, the reaction mixture was stirred for two hours at −78° C. and then alllowed to come to room temperature. After one hour at room temperature, the flask was placed under aspirator vacuum to remove excess phosgene and emptied to remove a white solid. The solid was dissolved in dichloromethane and evaporated to a colorless oil. The oil turned to a white solid (2.3 g), and this solid was extracted with dichloromethane, filtered and evaporated to an oily solid (0.62 g). An IR analysis of this material showed a rather large peak at the C—O—C area and also the carbonyl typical of a chlorocarbonate. Mass spectra indicated little if any of the desired chlorocarbonate but showed a very large peak at 376 which is exactly correct for the bis product, i.e., the compound

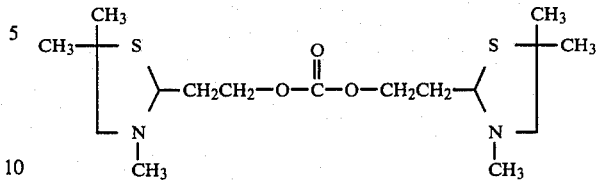

The hydroxyethyl-thiazolidine compound used as the starting material in the above Example was prepared as follows:

(1) Sodium metal (5.8 g; 0.25 mole) was added slowly to 80 ml of absolute ethanol contained in a one liter three-necked flask fitted with a dropping funnel, condenser, magnetic stirrer and nitrogen inlet. When all the sodium had dissolved, 100 ml of dry ether was added. Then a solution of ethyl propiolate (25 g; 0.25 mole) in 100 ml of ether was placed in the dropping funnel and added dropwise to the sodium ethoxide solution at a rate sufficient to keep the ether boiling. During this addition, the contents of the flask turned amber in color. After the addition was complete, the reaction mixture was stirred for 20–30 minutes, then poured into water and extracted with 200 ml ether (2x). The combined ether extracts were dried over sodium sulfate, filtered and evaporated to an oil. Distil. boiling range 90°–92° C. at 12 mm (lit. 206° C. at 754 mm). Yield of ethyl-3,3-diethoxypropionate 40 g; 85% by weight.

(2) A three liter three-necked flask, condenser and addition funnel were dried in an oven at 140°–150° C. overnight, assembled hot and cooled under a flow of dry nitrogen. Lithium aluminum hydride (7.2 g; 0.19 mole) and 800–900 ml of ether were placed in the flask with a magnetic stirring bar and the slurry was stirred vigorously. A solution of ethyl-3,3-diethoxypropionate (35 g; 0.184 mole) dissolved in 100–200 ml of ether was added to the lithium aluminum hydride slurry at a rate sufficient to keep the stirred slurry boiling. When addition was complete, the reaction mixture was refluxed for twelve hours. After cooling, 200 ml of water was added very cautiously with stirring and then carbon dioxide was bubbled into the mixture for two hours to hydrolyze the salts. The reaction mixture was filtered and the solids were washed several times with ether. The ether layer was separated, dried over sodium sulfate and evaporated to a colorless oil. Boiling range 85°–87° C. at 10 mm (Lit. 90°–92° C. at 10 mm) yield of 3-hydroxypropanal diethyl acetal 22 g; 85% by weight.

(3) 3-hydroxypropanal diethyl acetal (6 g; 0.04 mole), 100 ml water and 3 g of Amberlite IRI20 ion exchange resin were combined in a 500 ml ground glass stoppered Erlenmeyer flask and stirred at room temperature. The conversion of the diethyl acetal to 3-hyroxypropanal was followed by TLC (silica gel, chloroform solvent, iodine visualization) until all of the starting material was gone which required about one hour. When the reaction was complete, the resin was removed by filtration and the aqueous filtrate was used directly in step 4.

(4) To the filtrate of step 3 was added 1,1-dimethyl-2-methylaminoethanethiol hydrochloride (12.5 g; 0.08 mole), and the resulting solution was allowed to stir at room temperature overnight. When the reaction was finished (24–48 hours is usually sufficient), the aqueous layer was saturated with sodium bicarbonate. The aqueous layer was extracted several times with ether and the ether extracts were dried over sodium sulfate, filtered and evaporated to a colorless oil. The oil was dissolved in a minimum volume of chloroform and placed on a silica gel column which had been poured from a slurry of silica gel (Woelm 32–63) in petroleum ether. The column was eluted with 70% chloroform in petroleum ether. (This procedure was more of a filtration than a chromatographic separation.) The first material eluted from the column comprises the desired product. The solvent was evaporated from this material to leave the title compound as an oil.

As noted above, the compounds of the present invention are useful as intermediates in the synthesis of photographically useful compounds. For example, the reaction of chlorocarbonates with compounds containing an alcoholic hydroxy group or a primary or secondary amino group is well known in the art, and the subject thiazolidine chlorcarbonates find particular utility for reaction with a dye or other reagent possessing a hydroxy or amino group to give an image dye-providing compound or other photographically useful reagent. As an illustration, the subject compounds may be employed in the preparation of the thiazolidine compounds forming the subject matter of copending U.S. patent application Ser. No. 500,391 of Roberta R. Arbree, James W. Foley and Frank A. Meneghini filed June 2, 1983, now U.S. Pat. No. 4,468,449. Rather than reacting a 2-(2'-hydroxyethyl)-thiazolidine with an isocyanate to give a compound that releases a photographically useful reagent as a carbamic acid, such compounds may be synthesized by reacting a chlorocarbonate of the present invention with the appropriate reagent containing a hydroxy or amino group to give the desired product. As an example, the compound of Example 1 may be reacted with o-nitroaniline in a conventional manner to yield an image dye-providing material of the formula

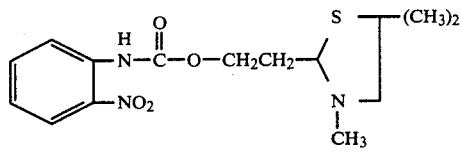

Since certain changes may be made in the herein-defined subject matter without departing from the scope of the invention herein involved; it is intended that all matter contained in the above description should be interpreted as illustrative and not in a limiting sense.

What is claimed is:

1. A compound of the formula

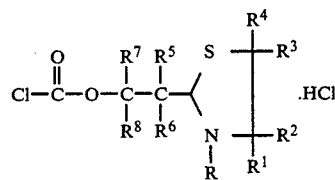

wherein R is selected from alkyl containing 1 to 20 carbon atoms, aryl selected from phenyl and biphenyl, phenyl-substituted alkyl wherein said alkyl contains 1 to 20 carbon atoms and alkyl-substituted phenyl wherein said alkyl contains 1 to 20 carbon atoms; $R^1$ is selected from hydrogen, carboxy, N,N-dialkylcarboxamido wherein each alkyl contains 1 to 20 carbon atoms, alkyl containing 1 to 20 carbon atoms, aryl selected from phenyl and biphenyl, phenyl-substituted alkyl wherein said alkyl contains 1 to 20 carbon atoms and alkyl-substituted phenyl wherein said alkyl contains 1 to 20 carbon atoms; $R^5$ is selected from hydrogen and carboxy; and $R^2$, $R^3$, $R^4$, $R^6$, $R^7$ and $R^8$ each are selected from hydrogen, alkyl containing 1 to 20 carbon atoms, aryl selected from phenyl and biphenyl, phenyl-substituted alkyl wherein said alkyl contains 1 to 20 carbon atoms, and alkyl-substituted phenyl wherein said alkyl contains 1 to 20 carbon atoms.

2. A compound as defined in claim 1 wherein R is alkyl.

3. A compound as defined in claim 1 wherein $R^1$ and $R^2$ are alkyl and $R^3$ and $R^4$ are hydrogen.

4. A compound as defined in claim 1 wherein $R^1$ and $R^2$ are hydrogen and $R^3$ and $R^4$ are alkyl.

5. A compound as defined in claim 4 wherein $R^5$, $R^6$, $R^7$ and $R^8$ each are hydrogen.

* * * * *